United States Patent [19]
Jackisch et al.

[11] Patent Number: 5,558,228
[45] Date of Patent: Sep. 24, 1996

[54] WATER-SOLUBLE POLYMER PACKAGING FOR DELIVERY OF INCOMPATIBLE CROP PROTECTION CHEMICALS

[75] Inventors: David A. Jackisch, Wilmington, Del.; David A. Styles, West Grove, Pa.

[73] Assignee: E.I. Du Pont de Nemours and Company, Wilmington, Del.

[21] Appl. No.: 338,514

[22] PCT Filed: May 20, 1993

[86] PCT No.: PCT/US93/04612

§ 371 Date: Nov. 28, 1994

§ 102(e) Date: Nov. 28, 1994

[87] PCT Pub. No.: WO93/23991

PCT Pub. Date: Dec. 9, 1993

[51] Int. Cl.⁶ ............................................. B65D 85/84
[52] U.S. Cl. ........................ 206/524.7; 206/219; 206/205
[58] Field of Search ................................... 206/219, 221, 206/524.7, 216, 205; 47/9.5, 48.5, DIG. 10

[56] References Cited

U.S. PATENT DOCUMENTS

| 2,091,993 | 9/1937 | Jones | 206/524.7 |
| 2,982,394 | 5/1961 | Novak | 206/46 |
| 3,273,704 | 9/1966 | Rudiger | 206/231 |
| 3,299,566 | 1/1967 | MacMullen | 47/1 |
| 3,676,363 | 7/1972 | Mosier | 252/316 |
| 3,695,989 | 10/1972 | Albert | 206/524.7 |
| 4,686,790 | 8/1987 | Lahalih et al. | 47/9 |
| 4,776,455 | 10/1988 | Anderson et al. | 206/.5 |
| 4,845,888 | 7/1989 | Lahalih et al. | 47/9 |
| 5,080,226 | 11/1992 | Hodakowski et al. | 206/205 |
| 5,222,595 | 6/1993 | Gouge et al. | 206/524.7 |

FOREIGN PATENT DOCUMENTS

| 0347222 | 12/1989 | European Pat. Off. . |
| 4113786 | 11/1991 | Germany . |
| 2095558 | 10/1982 | United Kingdom . |
| WO91/05714 | 5/1991 | WIPO . |

*Primary Examiner*—David T. Fidei

[57] ABSTRACT

Packaging of water-soluble polymer film is provided wherein crop protection chemical is dispersed within the thickness of the film, and the resultant film is either formed into a container to hold an incompatible crop protection chemical or laminated to another film within which is dispersed an incompatible crop protection chemical.

2 Claims, 1 Drawing Sheet

WATER-SOLUBLE POLYMER PACKAGING FOR DELIVERY OF INCOMPATIBLE CROP PROTECTION CHEMICALS

CROSS-REFERENCE TO RELATED APPLICATION

This application is a continuation under 35 U.S.C. 371 of international application PCT/US93/04612, with an international filing date of May 20, 1993, and international priority based on U.S. application Ser. No. 07/891,382, filed May 29, 1992, now abandoned.

BACKGROUND OF THE INVENTION

The present invention relates to the use of water-soluble polymer packaging for crop protection chemicals.

The concept of delivering a single agricultural chemical in a water-soluble polymer is addressed in U.S. Pat. No. 3,299,506 and British Patent 2,095,558. Each of these patents disclose a water-soluble polymer containing a uniformly dispersed chemical. The water-soluble polymer containing a chemical is formed into a thin film which can be torn or cut into measured sections for delivery of the chemical contained in the water-soluble polymer. The chemical is applied by placing the film on the ground or by adding the film to a predetermined amount of water in a sprayer. By these methods, the user is able to avoid contact with the chemical.

It is often advantageous, however, to spray a field or garden plot with more than one chemical at the same time. For example, one chemical would kill broadleafed weeds while another chemical would kill grassy weeds.

The problem of delivering incompatible crop protection chemicals has in the past been solved by delivering the chemicals in separate containers. Another solution has been the "twin pack" container which has two compartments for containing while physically separating two incompatible chemicals which are to be delivered simultaneously. These containers have the disadvantage that the container(s) must be rinsed and then subjected to disposal.

SUMMARY OF THE INVENTION

The present invention provides packaging for simultaneous delivery of incompatible crop protection chemicals to a field or garden plot. For purposes of this invention, incompatible chemicals are those which when placed in contact with each other will cause one or both of the chemicals to decompose.

The present invention takes advantage of the unique ability of a water-soluble polymeric film to encapsulate and immobilize a chemical, to provide a means for simultaneously delivering incompatible chemicals. The container for the incompatible chemicals is the water-soluble film. Since the container is water-soluble, there is no need for rinsing and disposal.

The present invention provides packaging for storing and releasing incompatible crop protection chemicals, comprising:

a) first and second crop protection chemical, said first and second chemicals being incompatible with respect to each other; and b) a container of water-soluble polymer film, said first chemical being encapsulated in said film and said second chemical being contained in said container; whereby upon solution of said film in water, said film and said container releases said first and second chemicals, respectively.

Another embodiment of the present invention is packaging for storing and releasing incompatible crop protection chemicals, comprising a plurality of water-soluble films laminated to one another, a first crop protection chemical being encapsulated in at least one of said films, and a second crop protection chemical incompatible with said first chemical being encapsulated in at least one other of said films so as to be stored separate from said first chemical, whereby upon solution of said films in water, said first and second chemicals are released into said water.

DETAILED DESCRIPTION OF THE INVENTION

Figure 1:
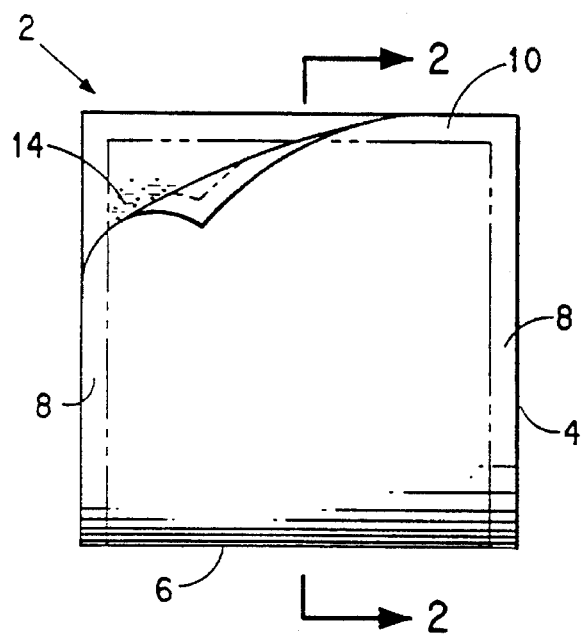
FIG. 1 shows a front view of one embodiment of packaging of the present invention with one film side of the packaging being peeled back to show the presence of crop protection chemical in the package.
Figure 2:
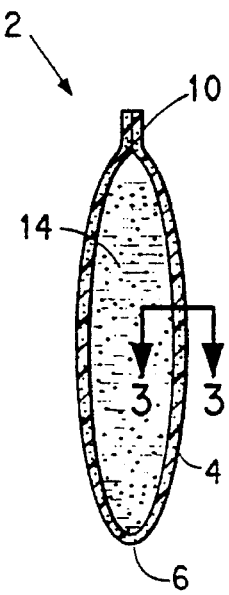
FIG. 2 shows a cross-sectional side view of the packaging of FIG. 1 with the thickness of the film forming the packaging being enlarged for the purpose of clarity.
Figure 3:
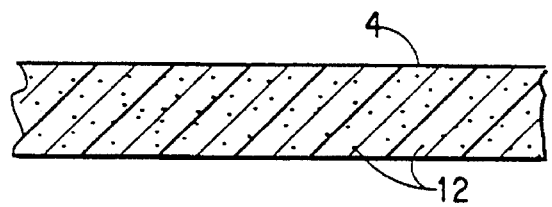
FIG. 3 shows an enlarged cross-section of the film of the packaging of FIG. 2, indicating the presence of crop protection chemical dispersed therein.

In FIGS. 1, 2, and 3, the packaging of the present invention is in the form of a pouch 2 (bag or envelope) made of water-soluble polymer film 4 by folding over the film upon itself to form a bottom 6 of the pouch and forming a heat seal closure of overlapping film portions along the sides 8 and top 10 of the pouch. The heat sealed overlapping film portions are best shown in FIG. 2 forming the top 10 of the pouch.

A dispersion of crop protection chemical 12 is encapsulated within the thickness of the polymer film 4 as best shown in FIG. 3. This dispersion is present throughout the film, even in the overlapping film portions forming the sides 8 and top 10 of the pouch.

The presence of polymer at both surfaces of the film as best shown in FIG. 3 serves as packaging for the crop protection chemical until the film is dissolved in water and provides a polymer surface for heat sealing overlapping film portions one to the other to form the packaging.

Instead of heat sealing to form the sides and top of the pouch 2 or other form of packaging, water wetting of the overlapping film surfaces to form packaging seals can be used, especially for water-soluble polymers which are not thermoplastic. When heat sealing is used, the heat sealing temperature will be just below the melting point of the polymer, sufficient to cause the overlapping film portions to fuse together under pressure to form the seal.

A second crop protection chemical 14 is contained within the pouch 2. This is added to the pouch after forming the heat seals along the side 8 of the pouch 2 and prior to forming the heat seal along the top of the pouch. Although the second crop protection chemical is incompatible with the first chemical encapsulated in the film 4 forming the packaging, the film encapsulation keeps these chemicals separate from and out of contact with each other.

Such packaging can be made in commercially available form, fill, and seal machines when film having crop protection chemical dispersed therein is first formed into a cylindrical shape, followed by sealing the longitudinal edges of the film to one another to form the side seal of the container, followed by pinching the cylinder and forming a bottom seal where pinched together, filling of the container with incompatible crop protection chemical, and then sealing the top of the resultant bag.

The size of the packaging will be dictated by the field area of application for the packaging. In the embodiment shown in FIGS. 1–3, the pouch is the size of an oversized tea bag. In use, the pouch is added to the tank of water used for splaying onto the field or plot. The residence time of the packaging in the tank is sufficient to allow the polymer film to dissolve, simultaneously releasing the stored chemicals 12 and 14 into the tank for spraying onto the field or plot (including any agricultural crop present thereon). Typically, the polymer is such that the film will dissolve within 15 minutes after being added to the water, which will generally be at a temperature of 2° to 20° C. Promptly after the film dissolves, the contents of the tank are sprayed onto the field or plot, prior to the chemicals 12 and 14 having any chance of appreciable degradation, either by reaction with one another or with the water present in the spray tank.

Figure 4:
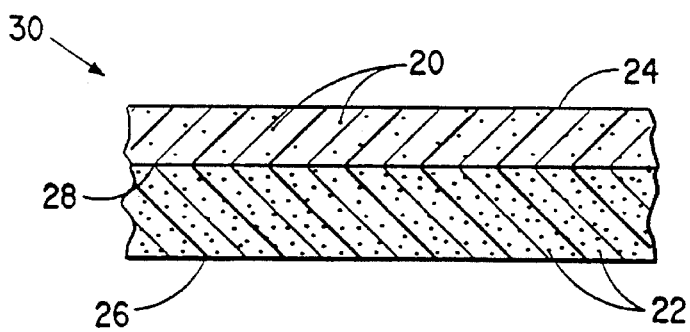
FIG. 4 shows an enlarged cross-section of another embodiment of packaging of the present invention.

In another embodiment of the present invention, shown in FIG. 4, the incompatible crop protection chemicals 20 and 22 are dispersed within and thereby encapsulated by water-soluble polymer films 24 and 26, respectively, which are laminated one to the other either via heat or moistening along line 28 representing the area of mutual contact between the films. The dispersion of crop protection chemical 22 is more dense than for chemical 20 and film 26 is thicker than film 24 as a way of providing a greater proportion of chemical 22 for the packaging 30 represented by this laminate. As in the case of pouch 2, when packaging 30 of the length and width desired is added to water in a spray tank, the films dissolve to simultaneously release the incompatible chemicals into the water for spraying.

Figure 5:
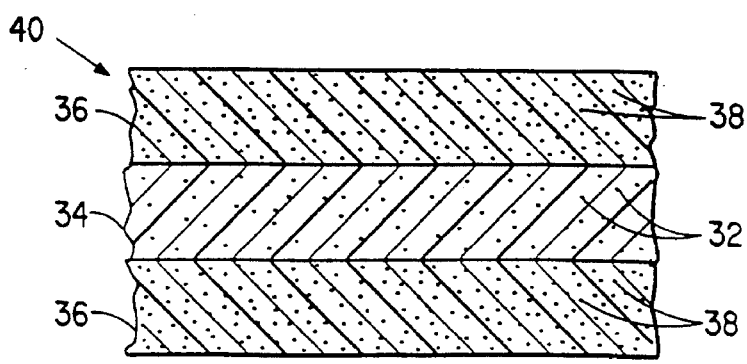
FIG. 5 shows an enlarged cross-section of still another embodiment of packaging of the present invention.

In a variation of the embodiment of FIG. 4, as shown in FIG. 5, one crop protection chemical 32 is dispersed within one layer of film 34, which is sandwiched between layers of film 36, within which are dispersed different crop protection chemical 38 which is incompatible with chemical 32. The three films are laminated together to form package 40 for the incompatible chemicals, wherein the relative proportion of chemical 38 to chemical 32 is varied (increased) by having multiple layers of film 36 of the same thickness encapsulating chemical The water-soluble polymer film used in the present invention may be of any suitable film-forming material such as polyvinyl alcohol, methyl cellulose, polymethylene oxide, sodium carboxy methyl cellulose, polyvinyl pyrrolidone or polyacrylamide selected in the film thickness used and particular form of packaging to form polymer film that is both sufficiently tough and flexible to withstand fabrication, filling, and handling.

Crop protection chemicals include insecticides, fungicides, herbicides, repellants, attractants, defoliaments, plant growth regulators, fertilizers, bactericides, micronutrients, and trace elements. Films may contain combinations of these chemicals together with surfactants, dispersants, emulsifiers, and wetting agents to assist in the release and water dispersability of the chemicals.

Examples of incompatible pairs of crop protection chemicals which can be used in the present invention include:
Incompatible Pairs
bensulfuron methyl and molinate;
2,4-D and thifensulfuron methyl;
2,4-D and Methyl 2-[[[[N-4-methoxy-6-methyl-1,3,5-triazine-2-yl)-N-methylamino]carbonyl]amino]-sulfonyl]benzoate;
2,4-D and metsulfuron methyl;
maneb or mancozeb and benomyl;
glyphosate and metsulfuron methyl;
tralomethrin and any organophosphate such as monocrotophos or dimethoate;
Bromoxynil and N-[[4,6-Dimethoxypyrimidine-2-yl)-amino]carbonyl]-3-(ethylsulfonyl)-2-pyridine-sulfonamide;
Bromoxynil and Methyl 2-[[[[(4-methyl-6-methoxy)-1,3,5-triazin-2-yl)amino]carbonyl]amino]sulfonyl]-benzoate;
Bromoxynil and Methyl 2-[[[[N-(4-methoxy-6-methyl-1,3,5-triazin-2-yl)-N-methylamino]carbonyl]amino]-sulfonyl]benzoate The water-soluble polymer film encapsulating crop protection chemical can be made by dissolving the polymer being used in water followed by addition of and mixing of the crop protection chemical therewith and removal of water to form a solid polymer film with the crop protection chemical dispersed therein. The crop protection chemical can be in the form of a high-melting solid, a liquid, a wax, a granule or a powder. If the chemical is a liquid, it can be added directly to the dissolved polymer. The combination results in an oil-in-water emulsion. A low-melting waxy solid can be heated above its melting point and added to the polymer solution. A powder can be added directly to the polymer solution or by making a slurry in water and adding it to the polymer solution. The combination results in a dispersion.

The resultant water-soluble film may contain from 1–75% of a crop protection chemical based on the weight of polymer plus crop protection chemical, to provide the amount of chemical desired for particular application while still having desired film physical properties.

The mixture of dissolved polymer and crop protection chemical can be cast into a film with, for example, a pressure die or a "doctor knife". The thickness of the wet cast film is adjusted to give the proper dry film thickness. The preferred thickness is from about 0.0003 to about 0.8 mm, preferably 0.03 to 0.3 mm. Typically, a continuous steel conveyer belt is used to support the film during drying. The finish can be matt or mirror finish so as to provide the required film handling properties. The film can be dried in a hot air oven and then stripped off the belt to form a roll. This roll is then slit into whatever width is required for the final packaging form.

Polymer solution temperature and oven temperature can be adjusted to a temperature that will ensure that the active ingredient does not decompose during processing.

The packaging of the present invention is unique in its ability to store and deliver two or more incompatible crop protection chemicals simultaneously. The encapsulated chemical is not available to any incompatible chemical. Therefore, degradation from contact with an incompatible chemical is prevented. An effective amount of each chemical for application to the crop or field is predetermined and so provided in the packaging so as to provide the desired crop protection benefit from each chemical.

Because of the water-solubility of the polymer film forming the packaging, it will be desirable to wrap or contain the packaging in a waterproof outer wrap such as a polyethylene bag In use, the packaging would be removed from the bag and then added to the spray tank and disgarding or re-using the overwrap bag.

By way of specific example of the practice of the present invention, the solution of the ester salt of 2,4-D is incompatible with metsulfuron methyl (sulfonylurea herbicide). When they are put together, the sulfonylurea decomposes. They are frequently used together because the 2,4-D kills some weeds that are not killed by the sulfonylurea. Also, the 2,4-D has a different mode of action and helps prevent the development of resistant weeds. The use rate of 2,4-D to control weeds in cereals (wheat, barley, oats) is 0.5 pint/acre (585 mL/ha). The use rate for metsulfuron methyl is 0.06 oz. a.i./acre (4.2 g a.i./ha). A 0.004 in. (0.01 cm) thick film that contains 0.06 oz. (50% a.i.) of metsulfuron methyl would make a bag that is 4 in. by 5.5 in. (10 cm by 14 cm). This size bag would have enough capacity to hold 0.5 pint of 2,4-D. To make the bag, polyvinyl alcohol is added to water (15% by weight of PVOH). The mixture is stirred well and heated to 90° C. When all the polymer is dissolved, it is allowed to cool to room temperature to form a viscous polymer solution. The metsulfuron methyl is weighed to equal the weight of the polymer in solution. It is stirred into the viscous polymer solution. The mixture is cast on a glass plate with a "doctor knife" and allowed to dry overnight at room temperature. The film is folded and heat sealed to give a bag resembling that of FIG. 1 that is 10 cm by 14 cm. The 2,4-D liquid is poured into the bag and the top of the bag heat sealed. The polyvinyl alcohol film of the bag should be protected from water before use so it must be stored in a waterproof outer wrap. Well known plastics and foil/paper combinations are acceptable for this purpose. When the farmer is ready to use the combination product, he merely tears open the outer wrap and throws the bag into the spray tank. It will take about 2–10 min. for the bag to dissolve depending on the temperature of the water.

Molinate is incompatible with bensulfuron methyl. When they are in contact with each other, the bensulfuron methyl, sulfonylurea herbicide decomposes. They are used together in rice paddies because the molinate kills grasses and the bensulfuron methyl kills broadleafed weeds. The molinate is used at a rate of 3 pints/acre (3500 mL/ha). The bensulfuron methyl is used at a rate of 1 oz. a.i./acre (70 g a.i./ha). An 0.022 in. (0.057 cm) thick water-soluble polymer film can contain 50% by weight of bensulfuron methyl. The area of the film for one acre would be 129 in ($6.45\ cm^2$). This film can be cut, folded, and sealed using heat or moistening of overlapping surfaces to produce a carton like that used for milk in the U.S. The carton would be 3 in. (7.6 cm) deep, 3 in. (7.6 cm) wide and 10 in. (25.4 cm) high. The top could be a gable top so that the liquid molinate could be added using existing packaging equipment. This size carton would be big enough to hold 3 pints of molinate. The carton could be contained within a foil/cardboard container of similar shape to provide shape stability to the film in its carton shape.

What is claimed is:

1. Packaging for storing and releasing incompatible crop protection chemicals, comprising:

a) first and second crop protection chemical, said first and second chemicals being incompatible with respect to each other; and b) a container of water-soluble polymer film, said first chemical being encapsulated in said film and said second chemical being contained in said container, wherein said first chemical is not in contact with said second chemical; whereby upon solution of said film in water, said film and said container releases said first and second chemicals, respectively.

2. Packaging for storing and releasing incompatible crop protection chemicals, comprising a plurality of water-soluble films laminated to one another, a first crop protection chemical being encapsulated in at least one of said films and a second crop protection chemical incompatible with said first chemical being encapsulated in at least one other of said films so as to be stored separate from said first chemical, whereby upon solution of said films in water, said first and second chemicals are released into said water.

* * * * *